United States Patent [19]

Sawamoto et al.

[11] Patent Number: 5,298,255
[45] Date of Patent: Mar. 29, 1994

[54] ANTITHROMBIC MEDICAL MATERIAL, ARTIFICIAL INTERNAL ORGAN, AND METHOD FOR PRODUCTION OF ANTITHROMBIC MEDICAL MATERIAL

[75] Inventors: Jiro Sawamoto; Yoshihito Takano; Yuzo Ezaki, all of Fuji, Japan

[73] Assignee: Terumo Kabushiki Kaisha, Tokyo, Japan

[21] Appl. No.: 746,803

[22] Filed: Aug. 14, 1991

Related U.S. Application Data

[63] Continuation of Ser. No. 427,643, Oct. 27, 1989, abandoned.

[30] Foreign Application Priority Data

Oct. 28, 1988 [JP]  Japan .................................. 63-270788
May 22, 1989 [JP]  Japan .................................. 1-129826
Sep. 26, 1989 [JP]  Japan .................................. 1-249752

[51] Int. Cl.$^5$ .................. A61K 37/547; A61F 2/00; A61F 2/06
[52] U.S. Cl. .................. 424/423; 424/94.64; 623/1
[58] Field of Search .................. 424/423, 94.64; 623/1

[56] References Cited

U.S. PATENT DOCUMENTS

| | | | |
|---|---|---|---|
| 3,723,244 | 3/1973 | Breillant, Jr. ...................... | 424/423 |
| 4,378,803 | 4/1983 | Takagi et al. ...................... | 424/423 |
| 4,442,655 | 4/1984 | Stroetmann ........................ | 424/423 |
| 4,526,714 | 8/1985 | Feijen et al. ...................... | 424/423 |
| 4,534,069 | 8/1985 | Kelman ............................. | 623/6 |
| 4,565,740 | 1/1986 | Gölander et al. ................... | 424/423 |
| 4,711,782 | 12/1987 | Okada et al. ...................... | 424/455 |
| 4,837,379 | 6/1989 | Weinberg .......................... | 424/423 |
| 4,979,959 | 12/1990 | Guire ............................... | 623/1 |
| 5,053,048 | 10/1991 | Pinchuk ............................ | 623/1 |

FOREIGN PATENT DOCUMENTS

| | | |
|---|---|---|
| 51-103190 | 9/1976 | Japan . |
| 52-142772 | 11/1977 | Japan . |
| 61-58196 | 12/1986 | Japan . |
| 2166977 | 5/1985 | United Kingdom . |
| 2187463 | 9/1987 | United Kingdom . |

OTHER PUBLICATIONS

*Journal of Cellular Physiology*, vol. 125, 1985, pp. 1-9-"Fibrin-Enhanced Endothelial Cell Organization" by J. V. Olander et al.
*Process in Artificial Organs-1983 Biomaterials*, pp. 852-857,-"Thermoplastic Elastomers for Small Diameter Compliant Grafts" by Paolo Giusti et al.
*Biorheology*, vol. 22, No. 3, 1985, pp. 197-208, "A New Rheological Method to Measure Fluidity Change of Blood During Coagulation: Application to In Vitro Evaluation of Anticoagulability of Artificial Materials" M. Kaibara et al.
*Thrombos. Haemostas*, vol. 42, No. 4, 1979 (pp. 1153-1158) "Fibrin Suspension as a Substrate for Plasmin: Determination and Kinetics" by Shozo Kanai et al.
*J. Lab. Clin. Med.*, vol. 97, No. 3, 1981, pp. 403-411, the C. V. Mosby Co., "Selective Immobilization of a α-thrombin by Surface-Bound Fibrin" by G. D. Wilner et al.
*Life Support Syst.*, vol. 3, (suppl 1, Proc.-Eur. Soc. Artif. Organs, Annu. Meet., 12th 1985, pp. 476-480) "New Biolized Polymers for Cardiovascular Applications" by P. Guisti et al.

Primary Examiner—Paul R. Michl
Assistant Examiner—Amy Hulina
Attorney, Agent, or Firm—Burns, Doane, Swecker & Mathis

[57] ABSTRACT

An antithrombic medical material, having superposed on the surface of a substrate formed of a polymer material a polymerized protein substantially free at least from erythrocyte and leukocyte, a medical device using the same, and a method for production of the antithrombic medical material.

7 Claims, 7 Drawing Sheets

ANTITHROMBIC MEDICAL MATERIAL, ARTIFICIAL INTERNAL ORGAN, AND METHOD FOR PRODUCTION OF ANTITHROMBIC MEDICAL MATERIAL

This application is a continuation of application Ser. No. 07/427,643, filed Oct. 27, 1989, now abandoned.

BACKGROUND OF THE INVENTION

1. Field of the Invention

This invention relates to a novel biocompatible material, particularly an antithrombic medical material excellent in resistance to thrombus and in tissue-biocompatibility and therefore useful in artificial blood vessels, artificial internal organs, and catheters, to artificial internal organs and artificial blood vessels using the medical material, and to a method for the production thereof.

2. Description of the Prior Art

In the field of medical materials, numerous synthetic polymer materials such as polyesters, polyethylene, polypropylene, and polyurethane have found utility and have been producing numerous appreciable results. When they are used as medical materials such as, for example, artificial blood vessels which are destined to be exposed directly to blood, they cause coagulation of blood and induce thrombus. For the solution of this problem, various devices have been developed for the impartation of antithrombic quality to these polymer materials. For example, a method which comprises chemically binding such a natural anticoagulant substance as heparin to the surface of a given material (Japanese Patent Laid-Open SHO 51 (1976)-103,190) and a method which comprises endowing a given polymer substance with a synthetic radiolytically active compound as 1,2-diphenyl-3 or 5-dioxypyrazoline derivative (Japanese Patent Laid-Open SHO 52 (1977)-(142,772) have been known to the art. The heparin now in use has no perfect biocompatibility because it is an anticoagulant substance mainly obtained from the internal organs of swine or other similar animals other than human beings. Moreover, the process of binding the heparin to a polymeric carrier entails an unsettled problem that the heparin is divested of its activity when it is joined to the polymeric carrier by virtue of a covalent bond. Efforts have been made for the solution of this problem. For example, the observation of highly preferable antithrombic quality exhibited by a polymer made to incorporate therein heparin by ionic bonding and applied in the form of a coating on the surface of a given polymer material has been reported in literature (Shoji Nagaoka et al, "Artificial Internal Organs," Vol. 17 No. 2, pages 598-601, 1983) and the fact that a ternary block copolymer, polystyrene-PEO-heparin, incorporating therein heparin as one of the microdomains was synthesized and tested for antithrombic quality has been reported (Vulic, I. Transactions of 13th Annual Meeting of Society for Biomaterials, Page 81, 1987). For use as artificial blood vessels, these materials are still short of practical utility and none of them prove to be satisfactory. Urokinase, a thrombolytic enzyme, is extensively utilized clinically as a medicine for thrombosis. In the blood in circulation, however, the action of urokinase is suppressed because such plasmin inhibiting factors such as $\alpha_2$-plasmin inhibitor and $\alpha_2$-macroglubulin are abundantly contained in the blood. It is not recognized to produce the effect expectable from its in vitro activity. It is known that beside the method for conferring antithrombic quality on the polymer materials, a method for rendering the materials themselves unsusceptible to thrombosis has been studied on a series of segmented polyurethane systems. The method of study by molecular design has been tried on the basis of the conventional trial and error method. Concerning microdomain polymers, the research has been approaching the point of clearly establishing the relation between their phase separating property and antithrombic quality (Atsushi Miyahara et al. "Glossary of Abstracts of 18th Medical Polymer Symposium," page 21, 1987). A method using porous polyurethane resin as a material has been studied (Martz, H. et al. "Biomaterials," 8. 3, 1987). In this case, the material has not yet been fully developed to the extent of deserving practical utility because the material, on being transplanted, either fails to induce the covering of intima or induces it only very slowly (Koichi Tamura et al. "Artificial Internal Organs," 16, 1500, 1987).

Concerning these studies, reports purporting generally to express that artificial blood vessels made of such materials are able to inhibit initial thrombosis and produce satisfactory results for brief periods following their transplantation but, during a protracted use over a period exceeding one month, they are more often than not clogged and that the clogging is ascribable to imperfect covering of intima have been published one after another (Shinichi Sato et al. "Journal of Japan Surgical Society," pages 89-109, 1988; Yoshitatsu Kubo et al. "Angiology," 27, 8, pages 567-571, 1987; Norio Morimoto et al. "Artificial Internal Organs," 14, pages 941-944, 1985; and Zempei Sakai et al. "Artificial Internal Organs," 15, pages 367-370, 1986). The view that the efforts relying solely on synthetic polymer materials for simultaneous impartation of antithrombic quality and early covering of intima therapy have their limits has come to prevail. In the circumstances, methods for positively promoting the covering of intima as what may be called hybrid type artificial blood vessels, e.g. a method which comprises superposing a collagen layer on the surface of a macromolecular material (Japanese Patent Publication SHO 61(1986)-58,196) and a method which comprises cross-linking to natural blood vessels polyglycerol-polyglycidyl ether (PGPGE) containing epoxy groups as reactive groups in the side chain and at the terminal thereof, are now under study. They have much yet to be developed in the future.

The use of conventional organs formed solely of natural tissues has a problem of kinetic nature that they undergo cancerous ampliation after a protracted retention in the living body. It also has the possibility of retarding the covering of intima because the use of heparin curbs the growth of cells (Wolfgang Laukes et al. "Biochem. J.," 251, pages 831-842, 1983).

The present inventors, in view of this true state of affairs, have continued a diligent study in search of a material which is dispossessed of the drawbacks suffered by the conventional antithrombic macromolecular materials, possessed of outstanding antithrombic quality and biocompatibility, and excellent in physical strength. Specifically, they have prepared model animals having injured intima in their blood vessels and continued a deliberate observation on the model animals to find how the blood vessels recover from the injuries. They have consequently found the conditions which the artificial blood vessels ought to fulfill. This invention has been accomplished on the basis of this knowledge. This knowledge is that when the intima of a natural blood vessel sustains an injury, one layer of fibrin formed on the exposed internal elastic lamina inevitably undergoes thrombosis and, thereafter, the blood vessel is not clogged but is allowed to induce the covering of intima in a matter of only one week's time. On the basis of this knowledge, the inventors have noticed the fibrin temporarily formed on the internal elastic lamina after infliction of an injury on the intima as a material combining antithrombic quality with early healing. They have perfected this invention as the result.

An object of this invention, therefore, is to provide a novel antithrombic medical material, an artificial internal organ, and a method for the production of a material for promoting antithrombic quality.

SUMMARY OF THE INVENTION

The object described above is accomplished by an antithrombic medical material, having superposed on the surface of a substrate formed of a polymer material a polymerized protein layer substantially free at least from erythrocyte and leukocyte.

This invention also discloses a material, wherein the polymerized protein layer is produced by treating a blood plasma-forming protein with a proteolytic enzyme. This invention also discloses a material, wherein the proteolytic enzyme is a thrombin or an enzyme possessing a thrombin-like action. This invention also discloses a material, wherein the polymerized protein is a fibrin. This invention also discloses a material, wherein the polymerized protein layer is a fibrin layer having at least the surface thereof hydrolyzed. This invention also discloses a material, wherein the substrate is a porous substrate.

The object described above is further accomplished by a medical device formed of an antithrombic material having superposed on the surface of a substrate formed of a polymer material a polymerized protein layer substantially free at least from erythrocyte and leukocyte.

This invention also discloses a medical device, wherein the polymerized protein layer is produced by treating a blood plasma-forming protein with a proteolytic enzyme. This invention also discloses a medical device, wherein the proteolytic enzyme is a thrombin or an enzyme possessing a thrombin-like action. This invention also discloses a medical device, wherein the polymerized protein is a fibrin. This invention also discloses a medical device, wherein the polymerized protein layer is a fibrin layer having at least the surface thereof hydrolyzed. This invention also discloses a medical device, wherein the polymerized protein layer is formed on the surface for contact with blood. This invention also discloses a medical device, wherein the medical device is an artificial blood vessel, a catheter, or an artificial internal organ.

The object described above is further accomplished by a method for the production of an antithrombic medical material, which comprises coating the surface of a substrate formed of a polymer material with a layer of a proteolytic enzyme and subsequently causing the layer of the proteolytic enzyme to contact a solution containing a blood plasma-forming protein.

This invention also discloses a method described above, wherein the proteolytic enzyme is a thrombin or an enzyme possessing a thrombin-like action and the blood plasma-forming protein is at least one member selected from the group consisting of fibrinogen, cryoprecipitate, and plasma.

The object described above is also accomplished by a method for the production of an antithrombic medical material, which comprises coating the surface of a substrate formed of a macromolecular material with a fibrin layer and subsequently treating at least the surface of the fibrin layer with plasmin.

This invention also discloses a method described above, wherein the substrate is in a tubular form, the fibrin layer is superposed on the inner surface of the tubular substrate, and at least the surface of the fibrin layer is trerated with plasmin.

EXPLANATION OF THE PREFERRED EMBODIMENT

Figure 1:
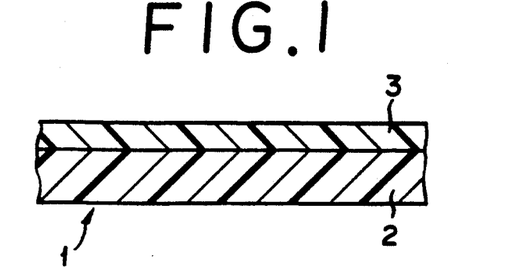
FIG. 1 is a schematic cross section of a typical antithrombic medical material as one embodiment of this invention.

Now, preferred embodiments of this invention will be described below with reference to the accompanying drawings. As illustrated in FIG. 1, an antithrombic medical material 1 of the present invention has superposed on the surface of a substrate 2 formed of a macromolecular material a polymerized protein layer 3 substantially free at least from erythrocyte and leukocyte.

The polymer substances which are usable for the formation of the substrate in the present invention include such synthetic polymer materials as nylon, polyesters, polyethylene, polypropylene, polyurethane, silicone, and polytetrafluoroethylene which are excellent in mechanical properties, and natural blood vessels, ureters, tissues and internal organs from living bodies, for example. Where a synthetic polymer material is used, it is desired to possess a porous texture from the standpoint of adhesiveness with respect to fibrin.

Figure 2:
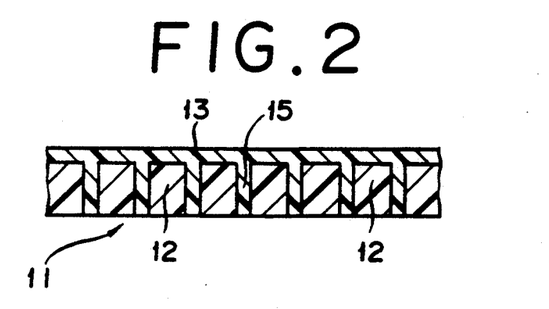
FIG. 2 is a schematic cross section of another embodiment of this invention.
Figure 3:
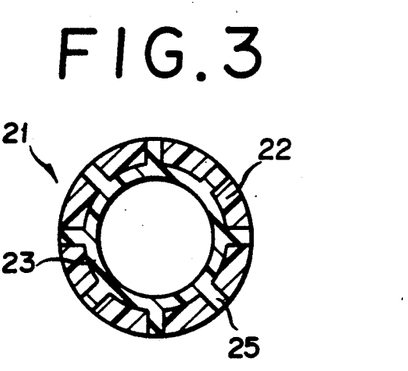
FIG. 3 is a schematic cross section of yet another embodiment of this invention.

Preferably, the porous polymer material is produced by the stretching process or the solid-liquid layer separation process, for example. The cross section of an antithrombic medical material 11 using a porous polymer substrate 12 is illustrated in FIG. 2. When this porous substrate 12 is used, since the protein mentioned above permeates pores 15 of the substrate and forms a protein layer 13 on the surface of the substrate 12, the fastness of adhesion of the protein layer 13 to the substrate 12 is improved. The cross section of an antithrombic medical material 21 using as a substrate 22 thereof a tubular article, particularly a porous tubular article formed of a polymer material, usable advantageously as an artificial blood vessel is illustrated in FIG. 3. In the case of this tubular article, similarly to the material of FIG. 2, since the protein permeates pores 25 of the tubular article and forms a polymerized protein layer 23, the fastness of adhesion of the protein layer 23 to the substrate 22 is highly satisfactory.

The polymerized protein substantially free at least from erythrocyte and leukocyte is what is obtained by treating a blood plasma-forming protein with a proteolytic enzyme. The expression "polymerized protein layer obtained by treating a blood plasma-forming protein with a proteolytic enzyme" means "what is formed by the contact of the two liquids, Liquid A and Liquid B, and what is substantially free from erythrocyte and leukocyte." Specifically, it refers to an immobilized "fibrin," which occurs when a fibrinogen comprising $\alpha$-, $\beta$-, and $\delta$-chains is reacted upon by thrombin, $Ca^{2+}$, or Factor XIII and finally cross-linked and converted into an insoluble fibrin. The term "Liquid A" is formed of a liquid whose main composition contains such a proteolytic enzyme as thrombin or an enzyme possessing a thrombin-like action represented by leptilase or snake venom. Optionally, Liquid A may suitably incorporate therein a calcium solution or Factor XIII, for example. The term "Liquid B" refers to a blood plasma-forming protein such as fibrinogen, cryoprecipitate, or plasma, for example.

The protein immobilized on the surface of the polymer material, as occasion demands, may be subjected to a cross-linking treatment by the conventional method.

The so-called "fibrin" of this invention which is obtained as described above, unlike the fibrin obtained by the conventional method, forms a monolayer texture betraying no unevenness and showing an intimate directionality under an optical microscope and is substantially free from erythrocyte and leukocyte.

The insoluble fibrin which is used in this invention as the final product of blood coagulation plays an important role during the course of treatment of wound healings. For the formation of granular tissues, the formation of an insoluble fibrin network due to the cross-linking proceeding between the individual fibrin molecules is an essential requirement (Hauktl. W. et al., "Thromb. Diath. Haemorrh., 32, pages 578–581 and Lorand L. et al., "Arch. Biohem Biophys, 105, pages 58–67, 1964). Since the thrombosis generally follows the course in which it is aggravated with blood components are gradually occluded in the fibrin network, the view that the fibrin lends itself to the aggravation of thrombosis is prevalent. What should be noted here in the fact that the fibers of fibrin in which the cross-linking reaction is proceeding and the fibers of fibrin in which the reaction has been completed are radically different in terms of texture. The fibrin, unlike the collagen, for example, is the kind of protein which is not physically present but is suffered to appear under unphysiological conditions. It is a substance which never fails to occur when the blood vessel is injured or when an artificial material is implanted in the living body.

Our study in search of the process for recovery of tissues from an inruty in model animals has led to a knowledge that the fibrin formed in the natural blood vessel immediately after infliction of an injury thereon is the very substance that can control the process of the healing of the tissues from the injury. The blood cell-rich so-called mixed thrombus contains numerous physiologically active substances such as arachidonic acid metabolite originating in blood, activated complement, and isozome enzyme and ought to be strictly discriminated from the fibrin which has issued from our study.

Since the seat of the fibrin has been found by our study with model animals to be converted by regeneration of intima into a substrate in a matter of only one week's time, since the observation of the in vitro contribution of fibrin to the formation of capillary blood vessels and the promotion of migration by endothelial cells has been reported in literature (J. Volander et al., "J. Cell Physiol., 125, pages 1 to 9, 1985), and further since the observation that owing to the fragmentation of fibrin, the hydrolyzates occurring at various stages possess various physiological activities and affect the migration and propagation of cells has been reported (Akiyoshi Ishida et al., "Arteriosclerosis," 8, page 605, 1981), the various physiological functions exhibited by the fibrin and the role discharged by the fibrin in the seat of inflammation justify the confident expectation that the fibrin will have a bright future as a medical material.

In addition to the behavior of the fibrin described above, we have found that the polymerized protein layer obtained by treating a blood plasma-forming protein with a proteolytic enzyme comprising fibers possessing a close directionality and form a flat smooth surface.

Preferably, the polymerized protein is fibrin. Further, in accordance with the present invention, the antithrombic material is produced by treating the surface of a substrate made of a polymer material and subsequently treating the surface with a solution containing a blood plasma-forming protein. In this case, the proteolytic enzyme is thrombin or an enzyme possessing a thrombin-like activity such as leptilase and the blood plasma-forming protein is desirably fibrinogen, cryoprecipitate, or plasma.

The method of this invention for the production of the antithrombic material is as follows. As a concrete example, the method for the immobilization of fibrin to a macromolecular material assuming the shape of a tube will be described below.

A thrombin solution containing a $Ca^{2+}$ solution (Liquid A) is placed in a syringe, for example, and is injected into the cavity of a porous tube of polyurethane. Where the macromolecular material has a porous texture, it is desired to apply pressure to the injected solution so that the solution will fill the pores wholly.

After the injection of Liquid A, a fibrinogen solution (Liquid B) in a concentration of not more than 6% is injected under pressure into the cavity of the tube and consequently brought into contact with Liquid A and cross-linked on the surface of the cavity of the tube. Consequently, a monolayer fibrin membrane is formed and immobilized. The upper limit of the fibrinogen concentration is fixed at 6% because the solution of a higher concentration is sparingly soluble and difficult of handling.

This reaction is desirably carried out in a buffer near neutrality. A HEPES buffer, for example, may be used advantageously.

The thrombin solution of $Ca^{2+}$ is used in a suitable amount. Specifically, the amount of the thrombin solution to be used is not less than 1 unit, preferably 50 to 500 units, per g of fibrin. If the amount of the thrombin solution is less than 50 units, the activity of the thrombin on the fibrinogen is not sufficient. The physical strength is saturated when the amount of the thrombin solution is about 350 units/ml. The effect of the thrombin solution no longer elevated when the amount of the thrombin solution increases past 500 units. It, therefore, suffices to use the thrombin solution in an amount of not more than 500 units.

The amount of the $Ca^{2+}$ solution to be used is not more than 5 m.mols per 100 ml of the fibrinogen solution. The $Ca^{2+}$ solution is saturated at the concentration of 5 m.mols. If the solution is added in any greater amount, the excess is wasted without bringing about any proportionate addition to the effect. Thus, the upper limit is fixed at 5 m.mols.

Optionally, Liquid A may incorporate therein a proteolytic enzyme inhibitor such as aprotinin and may further incorporate therein a suitable amount of Factor XIII.

It is permissible to use such a blood plasma-forming protein as cryoprecipitate or plasma in the place of Liquid B. When the monolayer protein membrane substantially free from erythrocyte and leukocyte is immobilized on the surface of the macromolecular material, this membrane imparts antithrombic quality to the macromolecular material and endows it with high bioadaptability.

The fibrin layer is preferable to have at least the surface thereof hydrolyzed. The fibrin layer having the hydrolyzed surface is obtained by the method which comprises treating the fibrin layer with a proteolytic enzyme. Plasmin can be used advantageously as the proteolytic enzyme. The fibrin is formed by subjecting fibrinogen to limited decomposition by the action of thrombin and consequently liberating fibrinopeptides A and B. To be more specific, the fibrinogen is hydrolyzed by the enzyme, thrombin, and consequently caused to liberate fibrinopeptide A (FPA) from the A $\alpha$-chain and fibrinopeptide B (FPB) from the B $\beta$-chain respectively of the peptide chain thereof and convert itself into a fibrin monomer. The fibrin monomer is coagulation polymerized into an unstable fibrin polymer (soluble fibrin polymer). By the active factor XIII which has been hydrolyzed by the thrombin and activated by the $Ca^{2+}$ ion, the $\gamma$ chains of the adjacent fibrin molecules are cross-linked in the presence of the $Ca^{2+}$ ion (the isopeptide bonding between the lysine residue and the glutamin residue) to give rise to a stable fibrin polymer (insoluble fibrin polymer). The fibrin layer contemplated by this invention is formed of this insoluble fibrin polymer.

The plasmin which is used for hydrolyzing this fibrin layer is a proteolytic enzyme and the substrate is fibrin and fibrinogen. This enzyme is said to sever the fibrin between the lysine, the 43rd amino acid, and the triptophan, the 44th amino acid. The hydrolyzate of fibrin with the plasmin possesses an antithrombin activity.

When the fibrin layer is treated with the plasmin, at least the surface of the fibrin layer is hydrolyzed. The hydrolyzed part of the layer is believed to be in such a state that the residue of the digestion by the plasmin of the $\alpha$, $\beta$, and $\gamma$ chains constituting the fibrin (fragments X, Y, D, and E of hydrolyzate) and the part not yet digested (unhydrolyzed part) are distributed in a mixed manner. The hydrolyzate is thought to occur richly in the surface region of the fibrin layer which has been exposed to the plasmin. It is believed that the proportions of the hydrolyzed part and the unhydrolyzed part present, the proportions of the fragments formed, and the states of presence of the hydrolyzed part and the unhydrolyzed part are varied by the time of the treatment with the plasmin and the enzymatic activity of the plasmin. The hydrolysis by the plasmin is desired, though not essentially required, to occur on the whole surface region of the fibrin layer. The hydrolysis of the fibrin layer is only required to occur in the surface region thereof which is allowed to contact the blood. The fibrin layer treated with the plasmin tends to swell from the volume existing before the treatment.

The antithrombic medical material of this invention possesses high antithrombic quality and tissue-bioadaptability owin to the fact that this material possesses the fibrin layer and the fibrin layer has at least the surface region thereof hydrolyzed. Particularly this material causes the propagation of cells highly satisfactorily. As the result of the extension of the cells, a collagen is produced and uniform covering of intima ensues as a whole. The internal membranes which are newly formed as described above are propagated and extended on the hydrolyzed fibrin layer and consequently enabled to substrate the collagen layer produced by regeneration of intima themselves for the fibrin layer and produce a coating not easily separated. In the region coated by the newly formed intima, therefore, the initially present hydrolyzed fibrin layer does not exist and the collagen produced by the newly formed intima exists instead.

The idea of superposing the fibrin layer and incorporating the hydrolyzed part therein in the present invention has originated from the finding that in the experiment conducted for the purpose of finding conditions the artificial blood vessel ought to fulfil by preparing model animals having injuries in their blood vessels and continuous a deliberate observation on the process of healing of the blood vessels from the injuries, the fibrin layer is temporarily formed on the internal elastic lamina exposed by the injuries inflicted upon the intima and is not suffered to clog the blood vessels but allowed to be converted into newly formed intima in a matter of only one week's time, the finding that the fibrin is presumably modified in the meanwhile by inflammatory cells, and the finding that the direct contact of blood with the fibrin modified by the enzyme actually brings about early regeneration of imtima.

The antithrombic medical material can be used for various medical devices having surfaces intended for contact with blood. The medical devices answering this description include artificial blood vessels which are artificial internal organs possessing a surface for contact with blood, catheters of the kind retained for a long time in the living body, artificial dialyzers, such artificial internal organs as blood bypasses, artificial blood vessels, and artificial lungs, and artificial internal organs to be implanted in the living body, for example.

The antithrombic medical material 1 of this invention can be produced as follows.

First, a substrate is produced with a polymer material. This substrate 2 is desired to be such that the fibrin layer 3 can be formed even inside the substrate and the formed fibrin layer 3 can be immobilized on the substrate 2. From this point of view, the substrate is preferable to possess a porous texture. When the substrate of hydrophilic quality is selected for the purpose of ensuring high affinity for the fibrinogen solution or the thrombin solution as the starting material for the formation of the fibrin layer, the fibrin layer 3 can be immobilized under highly preferable conditions.

Then, the fibrinogen solution is prepared by using refined fibrinogen, plasma, or cryoprecipitate. The substrate mentioned above is then brought into contact with the thrombin solution to hydrolyze the fibrinogen with the thrombin on the surface of the substrate and, when the substrate has a porous texture, even inside the substrate and give rise to a fibrin layer on the surface of the substrate.

Subsequently, the substrate having the fibrin layer on the inner wall surface thereof is exposed to the plasmin solution. Though the time of treatment with the plasmin (the time of contact between the plasmin solution and the fibrin layer) is variable with the concentration of the plasmin in the plasmin solution, it is generally in the range of one second to 24 hours, preferably 5 to 15 minutes. When the plasmin concentration is 0.05 $\mu$/ml, for example, the time is preferable to be about 15 minutes. Then, the enzymatic reaction is stopped by the addition of a soybean trypsin inhibitor or an antiradiolytic agent to the plasmin solution. The treated substrate is given thorough rinse with physiological saline solution. Consequently, the antithrombic medical material of this invention provided with the fibrin layer having a hydrolyzed surface is obtained.

Now, the production of the antithrombic material of this invention will be described below with reference to working examples. It should be noted, however, that this invention is not limited by the following examples.

EXAMPLE 1

Method for immobilization of fibrin membrane

Figure 4:
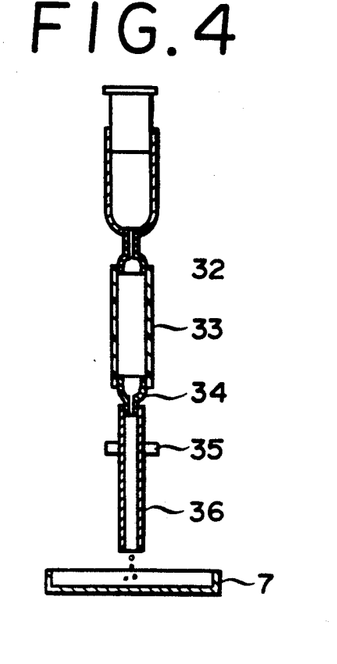
FIG. 4 is cross section illustrating a structure to be used in the method of this invention for the immobilization of fibrin on a tubular article.

In a syringe, 5 ml of a 50 $\mu$/ml pharmacopoeial grade thrombin solution (produced by Mochida Pharmaceutical Co., Ltd.) containing 3 m$\mu$ of $CaCl_2$ was prepared as Liquid A. Separately in a syringe B, 5 ml of a 3% human fibrinogel solution (produced by Midori Cross Corporation) was prepared as Liquid B. Then, in a device configured as illustrated in FIG. 4, the treatment of this invention was given to the inner wall surface of a tubular article 33 of porous polyurethane connected to a syringe 31 (cylinder) and a connector 32. The liquid A was injected under downward pressure into a tubular elastic article 33 of porous polyurethane (produced by Kanebo Ltd.) with the cylinder 31 and discharged through a tube 36 into a petri dish 37 by the manipulation of a clamp 35. Then, the liquid B was similarly injected to form a monolayer fibrin membrane on the surface of the cavity of the polyurethane tube 33. The fibrin membrane thus formed was left standing at rest for five minutes, then washed with 20 ml of physiological saline solution to remove the excess reaction solution, to obtain a fibrin membrane-immobilized tube.

EXAMPLE 2

Method for cross-linking immobilized fibrin

The fibrin membrane-immobilized tube obtained in Example 1 was treated as immersed in a physiological saline solution containing 0.1% glutaraldehyde, to obtain a fibrin membrane-immobilized tube having the fibrin membrane bound more strongly thereto. The tube was thoroughly washed and tested for antithrombic quality by the circulation process to be described specifically hereinafter. At the end of three hours' circulation test, the tube showed virtually no sign of adhesion of erythrocyte.

Ex vivo circulation test for evaluation of antithrombic quality

Figure 5:
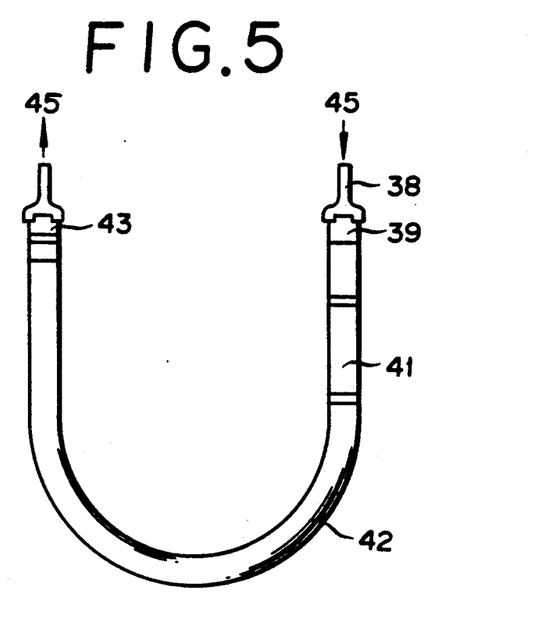
FIG. 5 is a diagram of a circulating circuit to be used in the test of an antithrombic material of this invention for AV shunt circulation in a rabbit, FIGS. 6(A) and (B) are photomicrographs illustrating the surface condition (particulate structure) of a monolayer fibrin membrane immobilized on the surface of a porous polyurethane substrate.

Healthy Japanese white rabbits (males and females weighing 2.3 to 3.0 kg) showing no conspicuous abnormality in a clinical examination were given general anesthesia by the injection of 25.92 mg/kg of pentobarbital through the auricular veins. The rabbits were tied on their backs to a bench and operated to expose their carotid arteries and jugular veins by the conventional surgical method. An A-V shunt circuit illustrated in FIG. 5, with the sample retained therein, was connected to the exposed carotid artery and jugular vein 45 through the medium of a 14 G retention needle (produced by Terumo Corporation and marketed under trademark designation of "SURFLO"), to start the circulation test. The blood of the animal was drawn from the carotid artery, led to the sample 41 through the retention needle 38 and the connector 39, passed through a transfusion set 42, then passed through a manifold tube 43 for sampling, and returned to the jugular vein 45. Immediately after the start of the circulation test, a sample of the blood was taken a sampling tube 43 of the circulation circuit and placed in a blood-collecting tube (produced by Terumo Corporation and marketed under trademark designation of "VENOJECT") containing EDTA-2K as an anticoagulant. The blood thus treated with the anticoagulant was tested with a blood platelet counter (produced by Ortho Instrument K.K. and marketed under product code of "ELT-8") to find the count of blood platelets. After 60 minutes', 120 minutes', and 24 hours' circulation, the blood was sampled and tested for the count of blood platelets in the same manner as described above. The ratio of decrease of blood platelets calculated in accordance with the formula, [Count of blood platelets after 24 hours' circulation]÷[count of blood platelets immediately after start of circulation]×100, was reported.

After the completion of the 24 hours' circulation test, the sample was removed from the circulation circuit, washed gentle with physiological saline solution, and then fixed with a 10% neutral buffer formalin solution. After the fixation, a paraffin segment was prepared from the sample by a method conforming, with necessary modifications, to the method for preparation of pathohistologic samples ("Method for Preparation of Pathohistologic Samples," compiled by Yonosuke Watanabe, 6th edition, published by Igaku shoin, 1986), stained with HE dye, and used for microscopic observation. As criteria of the evaluation, the behavior of thrombosis and the thickness of thrombosis formed were determined. The determination of the thickness of thrombosis was accomplished by photographing 8 points of thrombosis through a microscope at 90 magnifications and measuring the thicknesses of thrombosis in the photographs. After the 24 hours' circulation test, the sample was observed under a scanning electron microscope (produced by Japan Electron Optics Laboratory Co., Ltd. and marketed under product code of "JSM-840") with respect to the condition of adhesion of thrombosis.

EXAMPLE 3

A human fibrinogen preparation (produced by Midori Cross Corporation and marketed under trademark designation of "Fibrinogen HT-Midori") was dissolved in distilled water and passed through a Lysine-Sepharose 4B Column (produced by Pharmacia) for removal of plasminogen (plasmin). The solution emanating from the column was tested for its plasminogen content with a tester (produced by Daiichi Kagakuyakuhin K.K. and marketed under trademark designation of "Test Team, PLG Kit") to confirm the absence of any detectable plasminogen content. The solution was further tested for fibrinogen content with a coagulation time tester (produced by Did Corp and marketed under trademark designation of "Data-fi"). The solution was concentrated by the freeze drying process to prepare a 3% human fibrinogen solution free from plasminogen. This solution was labeled as Liquid B. Separately Liquid A was prepared by dissolving a pharmacopoeial grade thrombin (produced by Mochida Pharmaceutical Co., Ltd.) in a concentration of 50 units/ml with 2 mM of $CaCl_2$, 2 mM of $MgCl_2$, and 5 mM of HEPES buffer (pH: 7.4) containing 150 mM of NaCl.

Figure 6A:
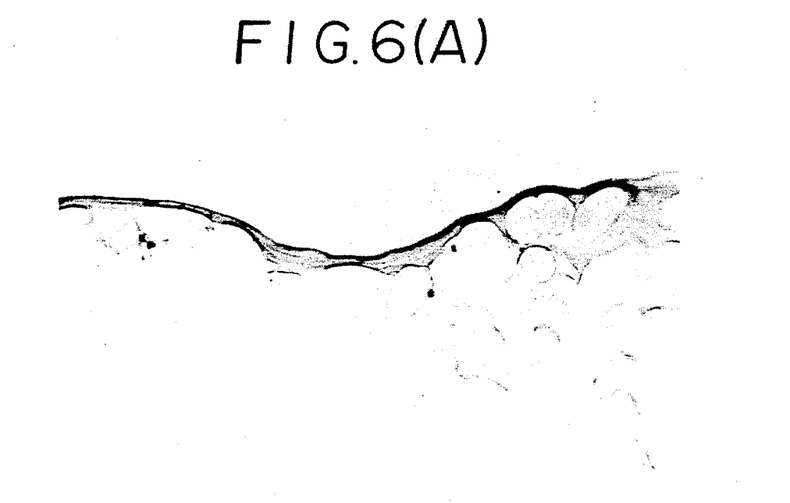
Figure 6B:
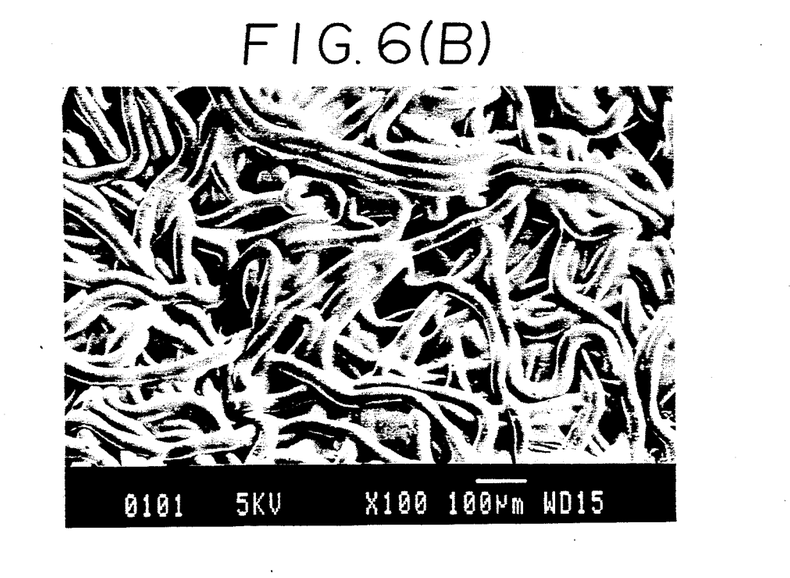

In a device configured as illustrated in FIG. 4, 3 ml of the liquid A was injected with a syringe into the cavity of the porous polyurethane tube (4 mm in diameter and 45 mm in length) used in Example 1 and 2.5 ml of the liquid B was similarly injected, to form a monolayer fibrin membrane on the surface of the cavity of the polyurethane tube. The tube thus treated was left standing at normal room temperature for a period of 5 to 10 minutes and was internally washed with 10 ml of physiological saline solution, to obtain a fibrin-immobilized tube. FIGS. 6(A) and (B) show photographs of the surface structures, taken under a microscope (100 magnifications), of a fibrin layer formed by this invention on the surface of a polyurethane substrate.

EXAMPLE 4

The plasminogen-free fibrinogen solution prepared in Example 3 was passed through a Gelatin-Cellulofine Column (produced by Seikagaku Kogyo K.K.) for removal of Fibronectin. The solution was treated with a tester (produced by TEFCO Corp and marketed under trademark designation of "SDS-Polyacrylamide Electrophoresis Device") to confirm the absence of a detactable band of Fibronectin. A 3% human fibrinogen solution deprived of plasminogen and fibronectin was prepared by following the procedure of Example 3.

A polyurethane tube coated with fibrin was produced by following the procedure of Example 3, using the fibrinogen solution prepared as described above.

When this fibrin-coated polyurethane tube was observed under an optical microscope and an electron microscope, it was confirmed that a monolayer fibrin membrane of flat and smooth surface was formed on the surface of the polyurethane substrate similarly to Example 3.

EXAMPLE 5

A tube of polyurethane having a fibrin membrane immobilized on the surface thereof by this invention and a comparative sample described below were subjected to the ex vivo circulation test in the same manner as in Example 2, using the fibrinogen solution obtained in Examples 3 and 4.

A total of 13 samples, i.e. three samples (A) of the material obtained in Example 3, two samples (B) of the material obtained in Example 4, three samples (C) of a porous elastic polyurethane article not coated with fibrin, three samples (D) of Gore-Tex (product of Gore-Tex Corp) ["Gore-Tex" is a commercially available Teflon type fiber material for artificial blood vessels, generally regarded as possessing antithrombic quality], and two samples (E), and two samples (E) not retained within a circulation circuit but incorporated only in a circuit, were subjected to the circulation test using 13 rabbits. The results were as shown in FIGS. 7 to 9 and Tables 1 and 2.

Figure 7A:
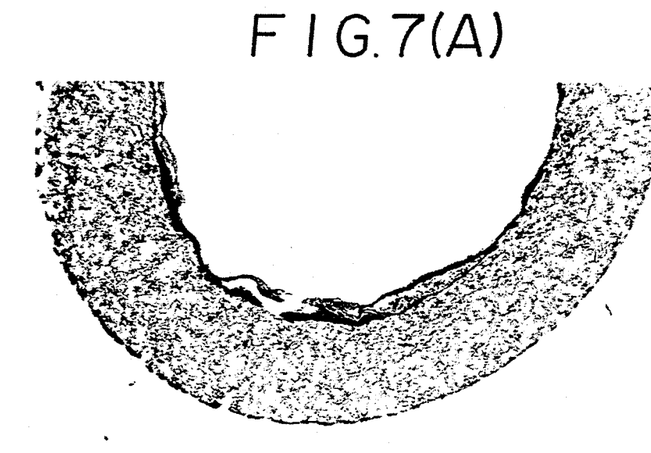
FIGS. 7(A) to (D) are optical photomicrographs of tissue segments illustrating the state and thickness of thrombosis after 24 hours' circulation test.
Figure 7B:
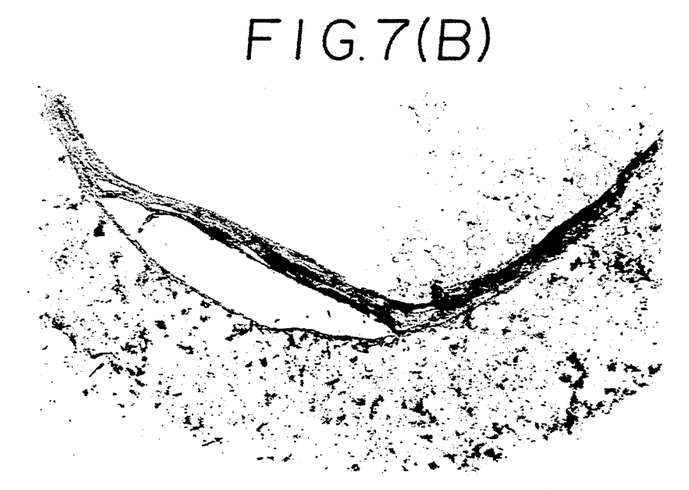
Figure 7C:
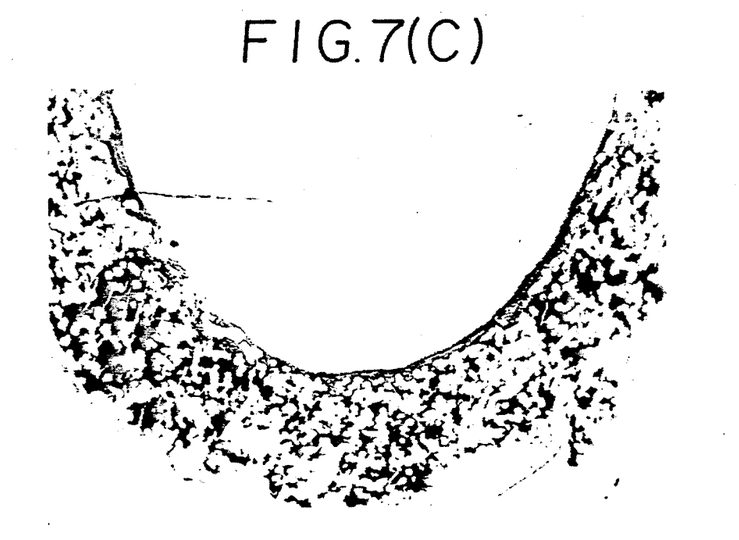
Figure 7D:
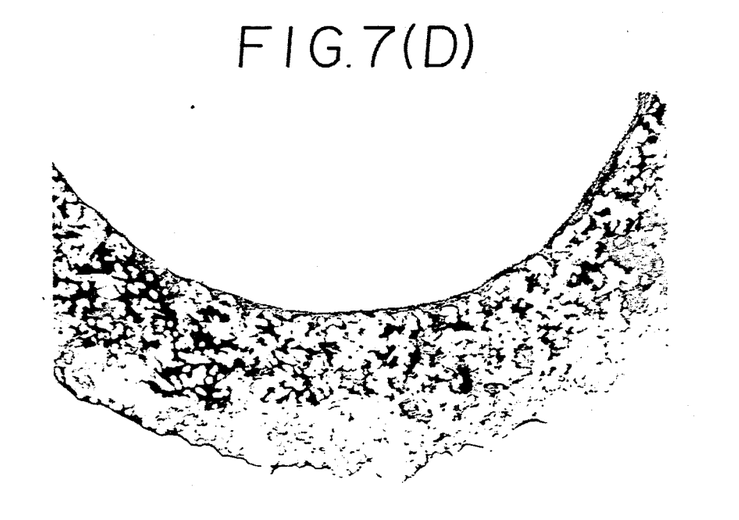

FIGS. 7(A), (B), (C), and (D) were photomicrographs (100 manifications) illustrating the surface structures of cavities respectively of the samples (A) to (D). The polyurethane surface having no fibrin coating, as shown in FIG. 4(C), formed a fibrin network possessing a coarse surface containing numerous red blood corpuscles. In contrast, the polyurethane surfaces coated in advance with a fibrin membrane as contemplated by this invention, as shown in FIGS. 7(A) and (B), were evidently smooth surfaces showing no sign of red blood thrombosis.

Figure 8A:
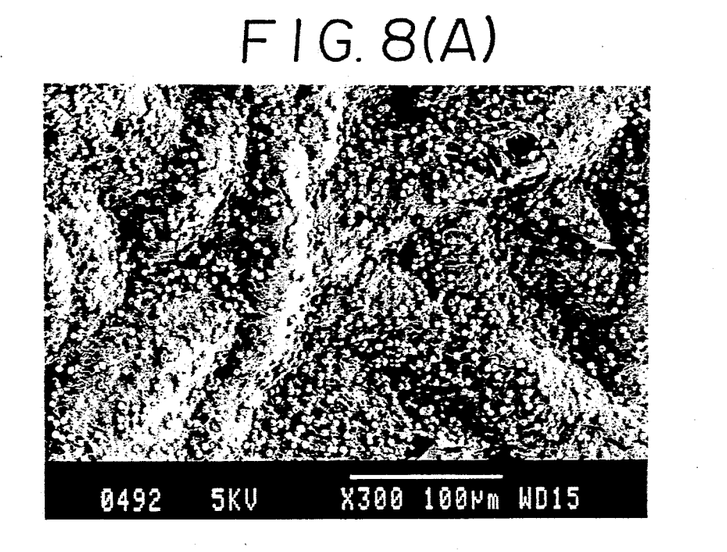
FIGS. 8(A) to (D) are photographs illustrating the particulate structure of surface taken through a scanning electron microscope.
Figure 8B:
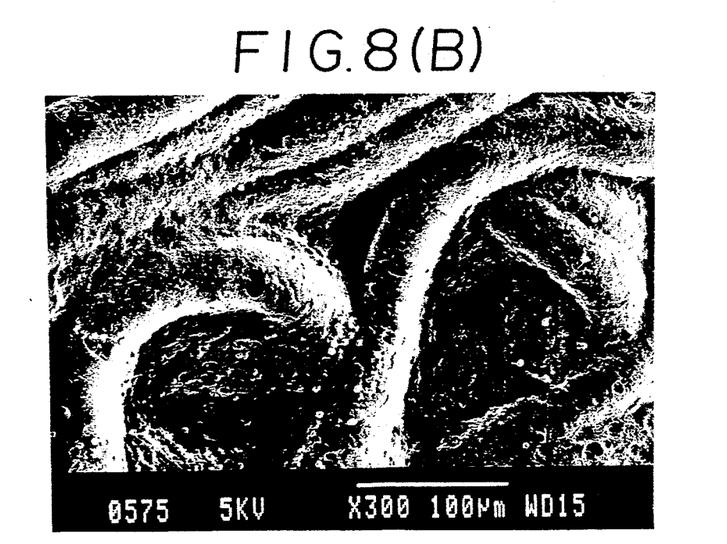
Figure 8C:
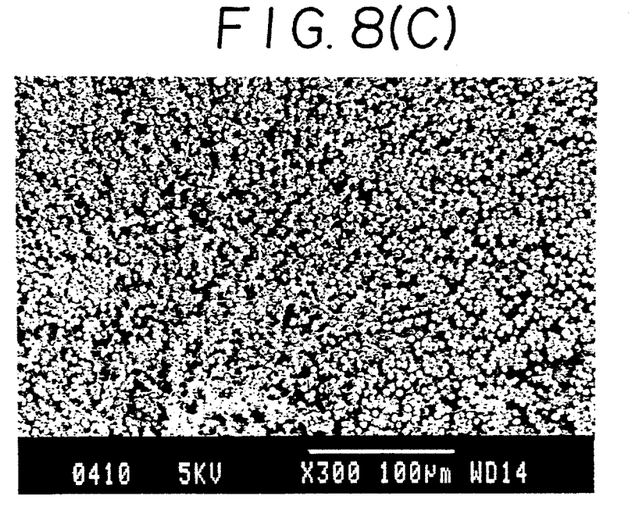
Figure 8D:
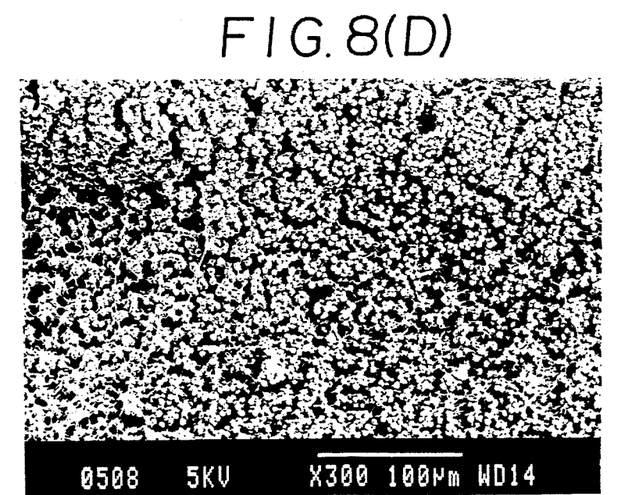
Figure 9:
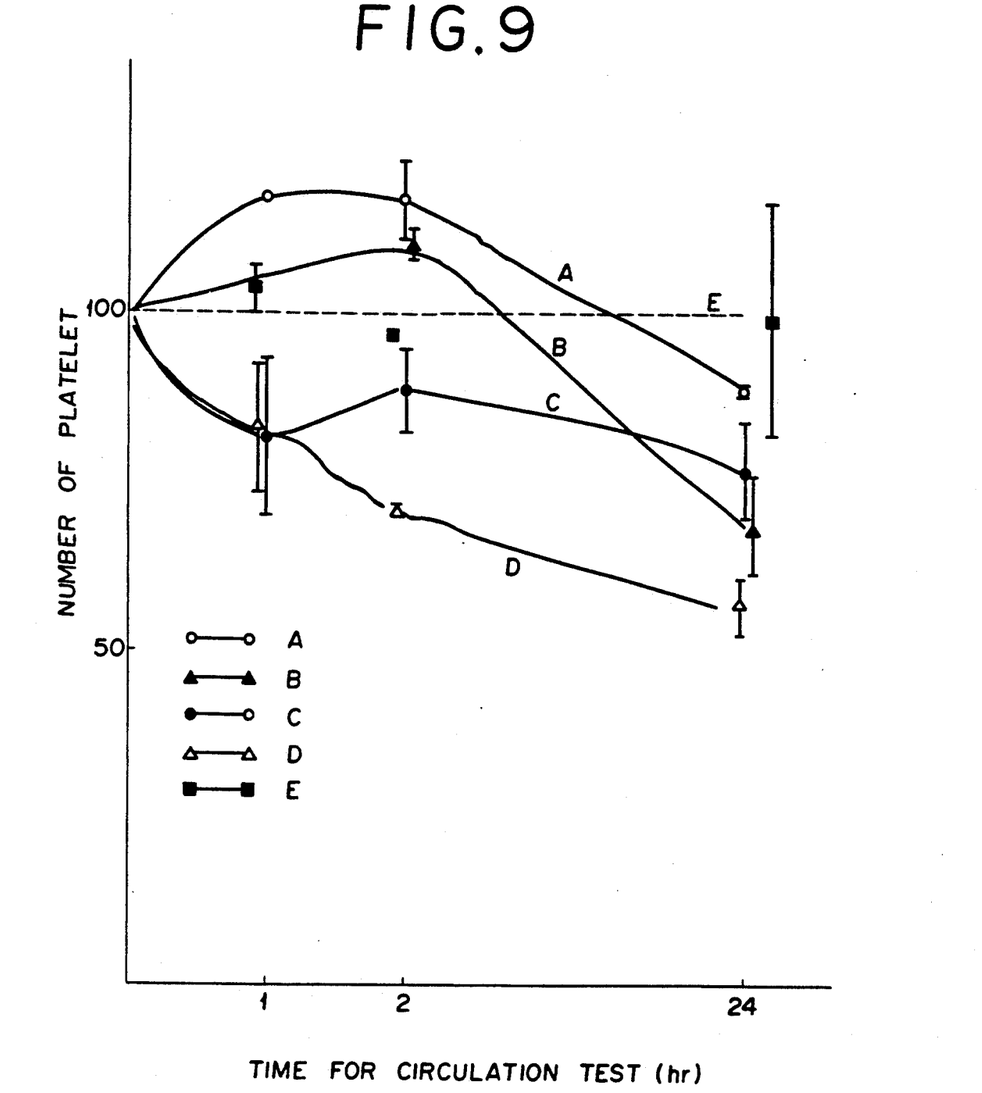
FIG. 9 is a graph showingh the change in the number of blood platelets along the course of time in a 24 hours' circulation test.

FIGS. 8(A), (B), and (C) were electron micrographs illustrating inner wall surfaces of polyurethane tubes. FIG. 4(D) shows Gore-Tex. The polyurethane tube having no fibrin coating clearly showed a fast fibrin network containing blood components richly [FIG. 8(C)]. In contrast, the polyurethane tubes having a fibrin coating barely showed a thin fibrin membrane containing virtually no red blood corpuscles [FIGS. 8(A) and (B)].

Table 1 shows a thrombosis points indicating amounts of adhering thrombosis obtained after 24 hours' circulation test. Group A, Group B, Group C, and Group D correspond to the samples of A to D mentioned above.

As shown in Table 1, Group A and Group B represent thrombosis points of polyurethane tubes having a fibrin coating and indicate that the adhesion of thrombosis was notably supressed and the amount of adhesion was notably small as compared with that of Group D, namely Gore-Tex.

TABLE 1

| | Thrombosis points found by test | | | |
|---|---|---|---|---|
| No. | Group A | Group B | Group C | Group D |
| 1 | 31 | 5 | 4 | 1 |
| 2 | 31 | 6 | 2 | 1 |
| 3 | 21 | 9 | 1 | 4 |
| 4 | 33 | 7 | 5 | 3 |
| 5 | 11 | 7 | 2 | 5 |
| 6 | 22 | 3 | 3 | 2 |
| 7 | 15 | 5 | 2 | 11 |
| 8 | 9 | 9 | 1 | 6 |
| 9 | 15 | 16 | 5 | 2 |
| 10 | 16 | 7 | 7 | 1 |
| 11 | 5 | 2 | 5 | 3 |
| 12 | 3 | 9 | 8 | 7 |
| 13 | 4 | 14 | 8 | 11 |
| 14 | 3 | 7 | 8 | 10 |
| 15 | 23 | 9 | 9 | 3 |
| 16 | 10 | 12 | 7 | 10 |
| 17 | 21 | 6 | 2 | * |
| 18 | 3 | 12 | 3 | * |
| 19 | 18 | 11 | 3 | * |
| 20 | 11 | 13 | 9 | * |
| 21 | 23 | 12 | 1 | * |
| 22 | 3 | 12 | 1 | * |
| 23 | 3 | 3 | 16 | * |
| 24 | 14 | 14 | 1 | * |
| Average | 14.5 | 8.8 | 4.7 | 5.0 |
| Standard error | 1.96 | 0.79 | 0.76 | 0.93 |
| Number of measurements | 24 | 24 | 24 | 16 |

Then, the samples A to D were kept under observation after the start of the circulation test as the decrease of blood platelet count in the blood. Immediately after the start of the test, after 60 minutes' test, 120 minutes' test, and 24 hours' test, the blood was sampled and examined to find the blood platelet count. The blood platelet counts found after elapse of the periods indicated above a were reported in percents, based on the blood platelet count found immediately after the start of the test taken as 100%.

TABLE 2

| | Change of blood platelet count (average value ± standard error) | | | |
|---|---|---|---|---|
| | After start | After 30 min. | After 120 min. | After 24 hrs. |
| A | 100 | 117.0 ± 0 | 116.0 ± 5.9 | 87.5 ± 0.5 |
| B | 100 | 98.0 ± 0 | 110.0 ± 2.0 | 67.0 ± 7.5 |
| C | 100 | 81.3 ± 11.5 | 88.3 ± 6.2 | 76.0 ± 7.0 |
| D | 100 | 83.5 ± 9.3 | 70.0 ± 2.0 | 56.0 ± 4.0 |
| E | 100 | 103.5 ± 3.5 | 96.5 ± 0.5 | 98.5 ± 17.5 |

In the table, E represents the circulation test performed only through the circuit, with no sample retained in the circulation circuit.

FIG. 9 graphically represents the data of Table 2. Specifically, it is a graph showing the ratios of decrease in the blood platelet count of the samples A to D, along the course of the time of circulation test.

It is noted from the data that in the samples involving the immobilization of fibrin (Curves A and B in the graph of FIG. 9), the decrease in blood platelet count was repressed as compared with the samples involving no immobilization of fibrin and further the decreases in blood platelet count were smaller than the sample of Gore-Tex (Curve D).

EXAMPLE 6

Preparation of fibrinogen solution

A human fibrinogen preparation (produced by Kabi Vitrum Corp. and marketed under product code of "Grade L") was dissolved in 50 ml of distilled water, passed first through a Geralin-Cellulofane Column (produced by Seikagaku Kogyo K.K.) and then through a Lysine-Sepharose 4B Column (produced by Pharmacia) for removal of Fibronectin and Plasminogen (plasmin), and thereafter passed through a steilized 0.20-um filter for sterilization. The fibrinogen solution resulting from the filter sterilization was treated by the coagulation time tester (produced by Dade Corp and marketed under trademark designation of "Data-Fi") to determine the concentration and then freeze dried. The freeze dried fibrinogen was dissolved in a concentration of 30 mg/ml with 20 mM of $CaCl_2$, 2 mM of $MgCl_2$, and 5 mM of HEPES buffer (pH 7.5) containing 150 mM of NaCl, to produce a human fibrinogen solution.

Formation of fibrin layer on substrate

In an e-PTFE graft tube 3 mm in inside diameter and 30 mm in length (porous stretched tube, produced by Gore-Tex Corp and marketed under trademark designation of "Gore-Tex"), 5 ml of a 50 units/ml thrombin (produced by Mochida Pharmaceutical Co., Ltd.) was injected under pressure and 2.5 ml of the aforementioned fibrinogen solution was injected under pressure. The treated tube was thoroughly washed with physiological saline solution and incubated at 37° C. for 24 hours, to produce a tube having a fibrin layer (5 μm in thickness) formed on the inner wall surface thereof. In the tube, the fibrin was found to have permeated the pores in the e-PTFE graft tube.

Treatment of fibrin layer for hydrolysis

The tube having a fibrin layer formed on the inner wall surface thereof as described above was immersed at 37° C. for 15 minutes in a 0.05 unit/ml plasmin solution prepared with 50 mM phosphate buffer, to expose the surface of the fibrin layer to the plasmin solution. Subsequently, soybean trypsin inhibitor (produced by Bohringer-Mannlein Yamanouchi K.K.) was added thereto in an amount calculated to yield a final concentration of 200 μg/ml, thorouhly washed with physiological saline solution, to form on the surface of the fibrin layer in the tube a hydrolyzed part resulting from the treatment with plasmin. Consequently, an artificial blood vessel (Example 6) was obtained.

The plasmin-treated fibrin layer was immobilized to the inner wall surface of the tube with relatively high fastness and could not be peeled under normal conditions. This plasmin-treated fibrin layer had a thickness of 20 um, indicating that this layer had been swelled from the thickness existing before the treatment.

The tube having the hydrolyzed fibrin layer formed on the surface thereof as described above (Example 6) and the tube provided with a fibrin layer not treated with the plasmin (Control 1) were stained by the hematoxylin-eosin dying method and observed under an optical microscope and an electron microscope. Consequently, in the tube of Control 1, a monolayer fibrin membrane was found on the inner wall surface of e-PTFE. In the tube of Example 6, though a similar layer was observed, this layer as found under the optical microscope was slightly swelled and stained undesirably as compared with the tube fibrin layer in the tube of Control 1.

EXAMPLE 7

An artificial blood vessel (Example 7) according with this invention was obtained by following the procedure of Example 6, except that a porous polyester tube (3 mm in inside diameter and 30 mm in length) formed of a plainweave of polyester fibers (75 deniers, 36 filaments) was used as a substrate.

EXAMPLE 8

An artificial blood vessel (Example 8 according with this invention was obtained by following the procedure of Example 6, except that a Golaski artificial blood vessel (3 mm in inside diameter and 30 mm in length) (produced by Golaski K.K.), an porous artificial vessel of polyester, was used as a substrate.

In the artificial blood vessels of Example 7 and Example 8, the plasmin-treated fibrin layers were immobilized to the inner wall surfaces of the tubes with relatively high fastness and could not be peeled under normal conditions. When the artificial blood vessels of Example 7 and Example 8 were stained by the hematoxylineosin dying method and observed under an optical microscope and an electron microscope, fibrin layers were found to be formed on the inner wall surfaces of the tubes. These layers as observed under the optical microscope were slightly swelled and stained rather unsatisfactorily as compared with the fibrin layer in the tube of Control 1.

CONTROL 3

The porous polyester tube used in Example 7 was immersed in 5 ml of whole blood in a sterilized container, left standing therein for five minutes. After the blood was coagulated, 5 ml of whole blood undergone an anticoagulant treatment with 1,000 u of heparin was injected into the cavity of the tube and the coagulated blood was removed. Subsequently, the cavity of the tube was further washed with physiological saline solution, to obtain an artificial blood vessel of Control 3.

CONTROL 4

An artificial blood vessel of Control 4 was obtained by treating the porous artificial blood vessel of polyester used in Example 8 in the same manner as in Control 3.

EXPERIMENT 1

The tube of Example 1, the tube of Control 1, and the untreated e-PTFE graft tube (Control 2) were transplanted end-to-end union in the aortas of rabbits (3 mm in diameter) and placed under continued observation as to the change along the course of time. Absolutely no anticoagulant such as heparin was used during and after the surgical operation. Seven samples of Control 2, five samples of Control 1, and nine samples of Example 6 were used in the experiment.

In the samples of Control 2 which had remained in rabbits for one month following the transplantation, the grafts were wholly red as observed with unaided eyes. In the histological examination of the grafts, the surfaces exposed to the blood except the portions showing an image of cellular migration from the opposite parts of union consisted mainly of blood components and contained no other cell. In the samples which had remained in rabbits for six months following the transplantation, virtually no neoplasm of internal membrane was recognized and an inclination of delaying the organization was recognized. In the samples of Control 1 and Example 1, the presence of cells constituting newly formed internal membranes was recognized in the centers of graft as early as only 15 days after the transplantation. The organization was attained more satisfactorily in the samples of Example 1.

When the samples were observed as to the condition of organization within the graft wall, the samples of Control 2 showed an inclination of delaying the invasion of wall interiors by cells, whereas the samples of Control 1 and Example 1 showed early invasion of wall inteiors by cells. The samples of Example 1 gave better results as a general trend than the other samples.

Further, the samples of Example 1, after 15 days following the transplantation, were covered with a substantially homogeneous collagen layer presumably indicative of the production of cells constituting newly formed internal membranes on the surface of the cavity of the tube. Even in the central part of the tube or at the parts of union, absolutely no sign of adhesion of thrombosis was recognized. Further in the samples of Example 1 after one month following the transplantation, complete substitution of cells was observed on the surface.

The results of Experiment 1 clearly indicate that in the artificial blood vesels of working examples of this invention, satisfactory propagation and extention of cells started from the opposite tubular parts of union and consequently produced a collagen and induced neoplasm of internal membrane on the entire inner wall surface of the tube.

EXPERIMENT 2

The artificial blood vessels of Example 2, Example 3, Control 3, and Control 4 were transplanted in end-to-end union in the aortas of rabbits (3 mm in diameter) and kept under continued observation as to the change due to substrate along the course of time. Absolutely no anticoagulant such as heparin was used during and after the surgical operation. During the course of the transplantation, no hemorrhage from the graft other than the parts of union was observed in any of the artificial blood vessels of Example 2, Example 3, Control 3, and Control 4. The anastomotic property and the sutural property were better in the sample of Example 2 using a knit fabric of polyester than that of Example 1 using e-PTFE substrate. The transplantation was conducted on two samples of Example 2, three samples of Example 3, three samples of Control 3, and two samples of Control 4.

After one month following the transplantation, congestion was recognized in two samples of Control 3 and one sample of Control 4. In the samples of Control 3 and Control 4 which remained uncongested for one month following the transplantation, conspicuous thromobosis in red was recognized. In the histological examination of these samples, the neoplasm of internal membrane was recognized only slightly and the artificial blood vessels were occupied with thrombosis in virtually all parts.

In the artificial blood vessels of Example 2 and Example 3, virtually no adhesion of thrombosis was recognized one month after the transplantation, the presence of cells constituting newly formed membrane was observed throughout the entire inner wall surfaces of the artificial blood vessels after the elapse of one month, and substantially homogeneous collagen layer presumably indicative of the production of cells constituting newly formed internal membrane was also recognized. From these results, it is clear that in the artificial blood vessels of Example 2 and Example 3, satisfactory propagation and extension of cells started from the parts of union in the tube and, consequently, induced the production of collagen and the formation of neoplasm of internal membrane throughout the entire inner wall surface of the tube. The results of this experiment indicate that the effect of this invention is brought about without being affected by the material of the substrate.

This invention is directed to a novel antithrombic material. In the medical field, as a material for use in parts destined to contact blood directly, an antithrombic material possessing mechanical strength and combining antithrombic quality with tissue-biocompatibility can be obtained by immobilizing on the surface of a polymer material possessing mechanical strength a fibrin membrane formed by an enzymatic reaction and containing substantially no red blood corpuscles or white blood corpuscles. Specifically, this invention provides an antithrombic material possessing excellent tissue-biocompatibility in addition to an ability to prevent blood from coagulating and aggravating thrombosis by a method which comprises immobilizing on the surface of a substrate a protein containing substantially no red blood corpuscle or white blood corpuscle and produced by polymerizing fibrinogen, cryoprecipitate or plasma as a starting material by the action of thrombin or an enzyme such as reptilase which possesses a thrombin-like activity.

Since the antithrombic medical material of this invention has on the surface of a polymer material a fibrin layer at least the surface region of which is hydrolyzed, it initially possesses antithrombic quality and prevents the adhesion of a thick vital tissue and the formation of thrombosis and, further, induces early substitution of vital cells for the regions exposed to blood and consequently effects satisfactory neoplasm of internal membrane. The fibrin layer defies separation and, owing to the neoplasm of internal membrane, exhibits a high antithrombic activity for a long time.

The antithrombic medical material, therefore, acquires semipermanent antithrombic quality and can be used for a long time in artificial blood vessels, blood vessel catheters, and artificial internal organs which by nature are required to contact blood for a long time.

The method of this invention comprises coating the surface of a polymer material with a fibrin layer and subsequently treating at least the surface of the fibrin layer with plasmin. Thus, the antithrombic medical material described above can be easily produced.

What is claimed is:

1. An antithrombic medical material which comprises a polymeric substrate, and a fibrin layer, the surface of which has been hydrolyzed by plasmin and is on the surface of said substrate.

2. The material according to claim 1, wherein said substrate is a porous substrate.

3. A medical device which is comprised of an antithrombic material which comprises a polymeric substrate and a fibrin layer, the surface of which has been hydrolyzed by plasmin and is on the surface of said substrate and which is substantially free of erythrocyte and leukocytes.

4. The medical device of claim 3, wherein said fibrin layer is positioned on the surface of the medical device which will come into intimate contact with blood upon in vivo implantation.

5. The medical device of claim 3, wherein said medical device is an artificial blood vessel.

6. The medical device of claim 3, wherein said medical device is a catheter.

7. The medical device of claim 3, wherein said medical device is an artificial internal organ.

* * * * *

UNITED STATES PATENT AND TRADEMARK OFFICE
CERTIFICATE OF CORRECTION

PATENT NO.  : 5,298,255
DATED       : March 29, 1994
INVENTOR(S) : Jiro SAWAMOTO et al It is certified that error appears in the above-identified patent and that said Letters Patent is hereby corrected as shown below:

In Column 15, line 65, delete "vesels" and insert -- vessels --.

Signed and Sealed this

Second Day of August, 1994

Attest:

BRUCE LEHMAN

Attesting Officer

Commissioner of Patents and Trademarks